United States Patent [19]

Blake, III

[11] Patent Number: 5,192,294
[45] Date of Patent: Mar. 9, 1993

[54] DISPOSABLE VASCULAR PUNCH

[76] Inventor: Joseph W. Blake, III, 88 Main St., New Canaan, Conn. 06840

[21] Appl. No.: 711,656

[22] Filed: Jun. 6, 1991

Related U.S. Application Data

[63] Continuation-in-part of Ser. No. 345,995, May 2, 1989, abandoned.

[51] Int. Cl.$^5$ .............................................. A61B 17/32
[52] U.S. Cl. .................................................... 606/184
[58] Field of Search ............... 606/167, 171, 184, 185, 606/174

[56] References Cited

U.S. PATENT DOCUMENTS

| | | | |
|---|---|---|---|
| 2,818,852 | 1/1958 | Kugler | 606/184 X |
| 3,776,237 | 12/1973 | Hill et al. | 606/174 |
| 3,835,860 | 9/1974 | Garretson | 606/184 X |
| 3,837,345 | 9/1974 | Matar | 606/171 X |
| 4,018,228 | 4/1977 | Goosen | 606/184 |
| 4,733,663 | 3/1988 | Farley | 606/171 X |

Primary Examiner—Robert A. Hafer
Assistant Examiner—David Kenealy
Attorney, Agent, or Firm—Lackenbach Siegel Marzullo & Aronson

[57] ABSTRACT

A surgical tool for cutting an opening in a blood vessel. The tool or punch has pistol-like housing, a blade pusher barrel at the front end thereof and reciprocally movable therein with a trigger for causing forward movement of the blade pusher barrel and a hollow blade drum. The hollow blade drum has a blade at its proximal end, which is inserted therein when an arm of the trigger is moved distally, whereby the blade enters and cuts the opening in the vessel. The barrel also contains a spring, behind the blade drum, which is compressed during the forward movement of the barrel. When cutting the opening the blade and proximal portion of the drum pass over a circular disc at the front of a non-movable punch mandrel contained within the hollow portion of the blade drum, the mandrel disc having been previously inserted into the vessel through an incision therein. Upon complete retraction of the trigger arm the trigger is locked in that position through engagement of complementary parts on the trigger and housing, so that barrel and blade drum are locked in their forward positions with the forward portion of the mandrel, and cutout tissue disc thereon, retained in the hollow portion of the blade drum. When recovery of the tissue is required the trigger is unlocked and the spring within the barrel permitted to expand thereby causing the barrel and blade drum to move distally, so that the front of the mandrel is exposed to permit removal of the tissue.

34 Claims, 15 Drawing Sheets

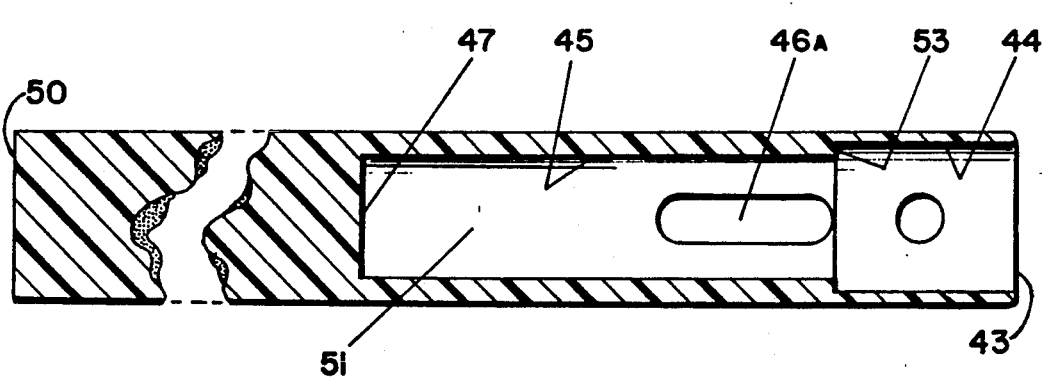
FIG. 8
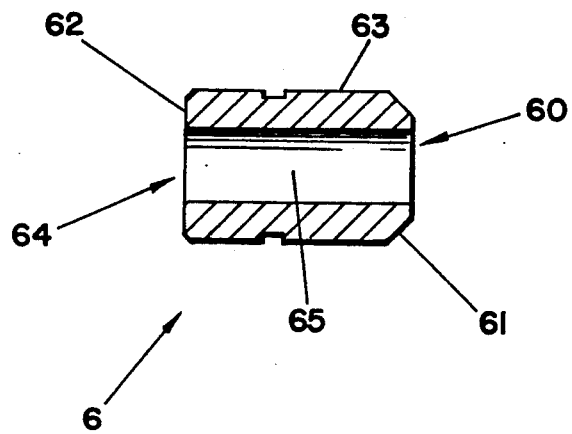
FIG. 9
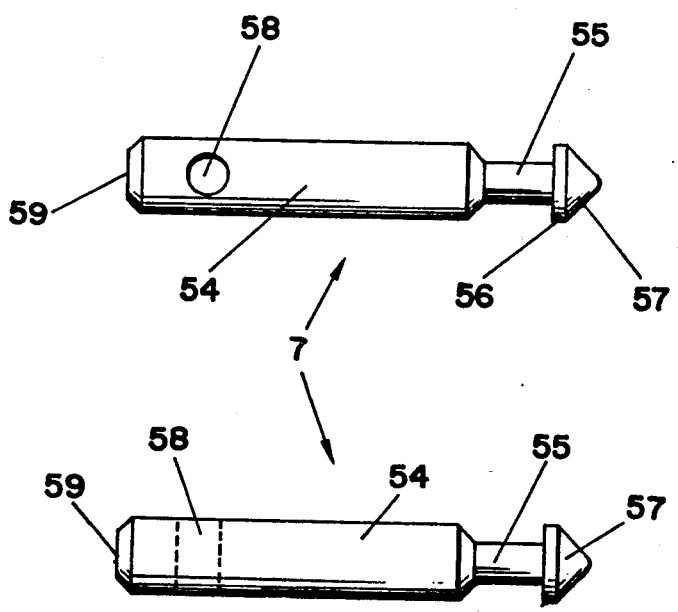
FIG. 10
FIG. 11

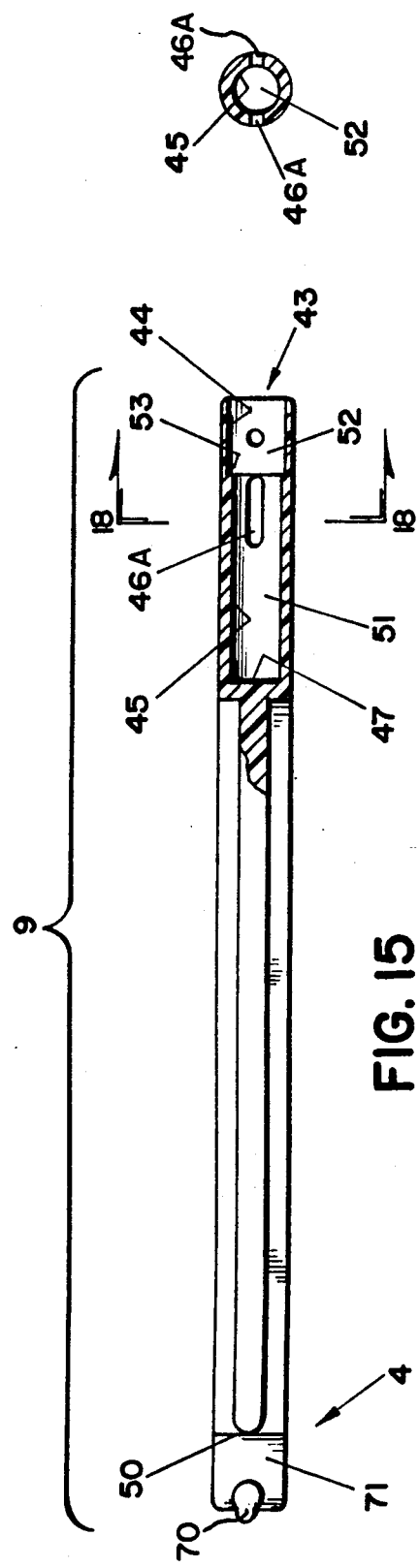
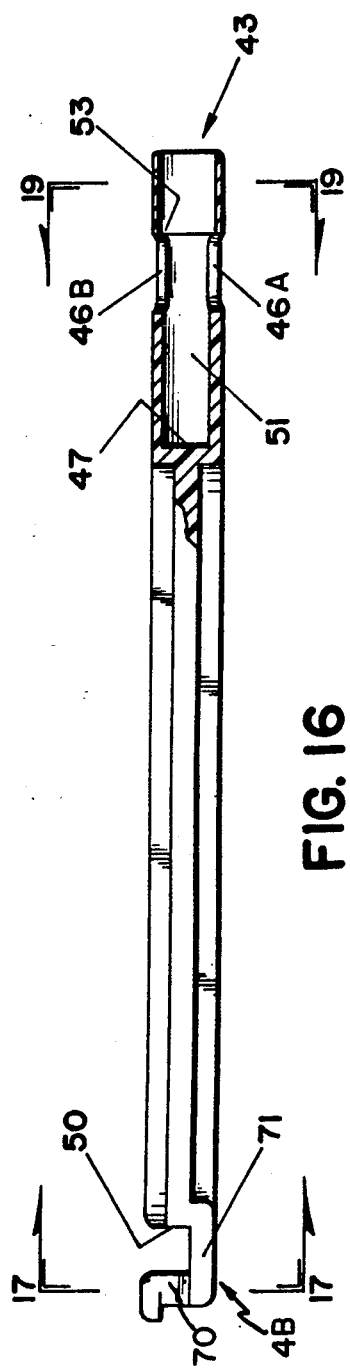
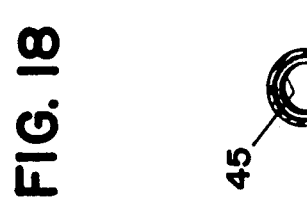
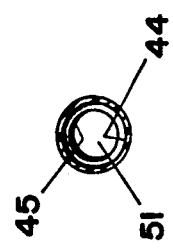

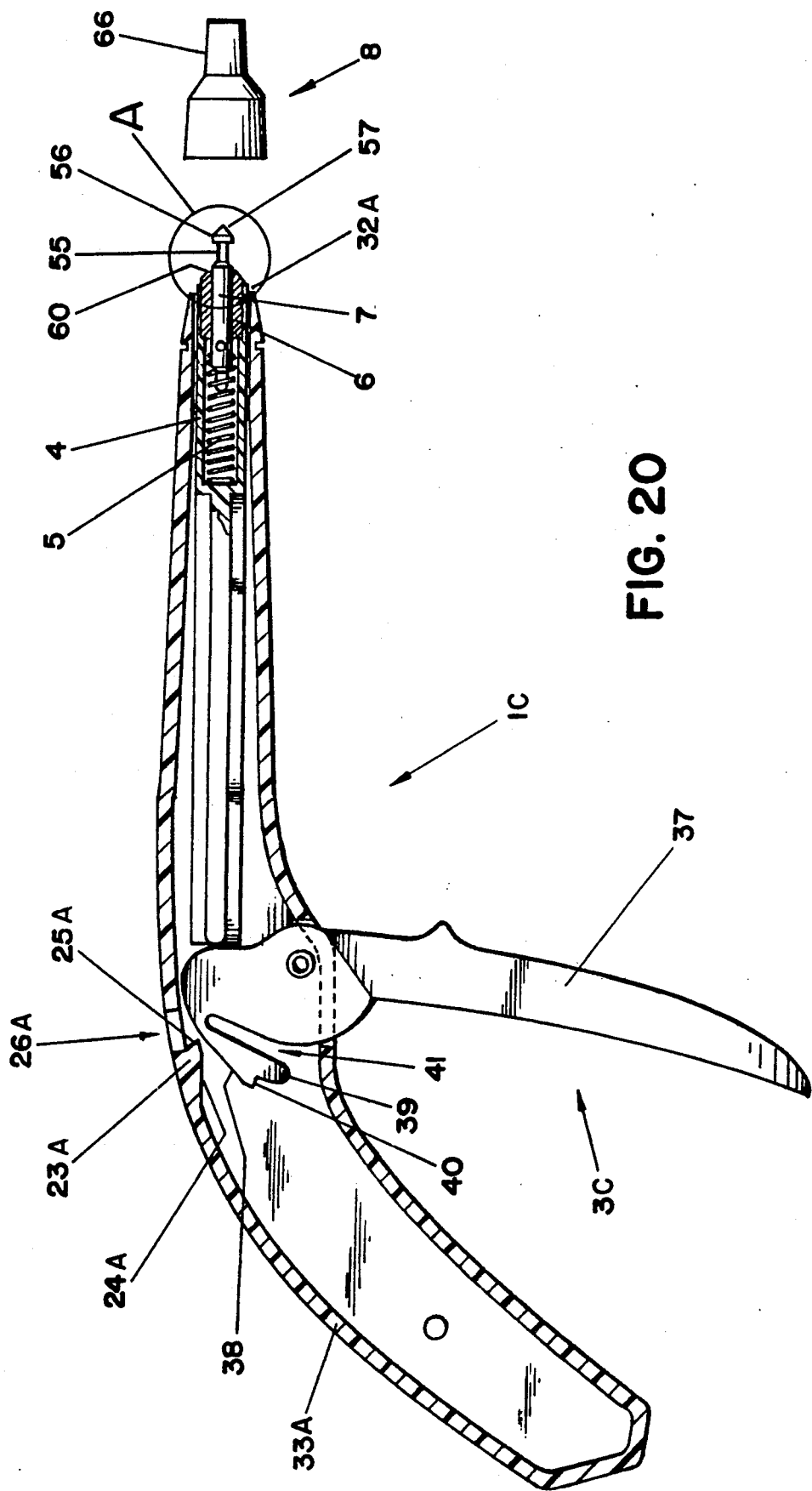

DISPOSABLE VASCULAR PUNCH

This is a continuation-in-part of Ser. No. 07/345,995 filed May 2, 1989, now abandoned.

FIELD OF THE INVENTION

The present invention relates to surgical instruments. More particularly it relates to a vascular punch, for forming uniform openings in body vessels such as aortae, having decreased manual force requirements and providing for safe retention of the removed vessel tissue.

In cardiac surgery it is often necessary to connect tubular items with blood vessels such as arteries and veins. Numerous prior art instruments for that purpose have been described, e.g., in U.S. Pat. Nos. 3,776,237 and 4,018,228.

The prior art instruments suffer, inter alia, from the following disadvantages:

1) large manual forces required to cut through the vessels; and
2) difficulty in stabilization of the instrument to form uniform smooth openings.

U.S. Pat. No. 4,018,228, for instance, describes an instrument comprising an elongated hollow sleeve and an elongated rod, extending through one end of the hollow sleeve and reciprocally movable therein. The elongated rod has a distal narrowed end portion comprising a fixed cylindrical blade while the hollow sleeve has a hollow cylindrical blade removably attached thereto. The sliding rod is activated by a handle attached normally thereto and extending through the slots in the elongated sleeve to move the rod proximally and pull the blade thereon into the hollow sleeve thereby forming an opening in the vessel tissue therebetween. The hollow sleeve further contains a spring proximal to the handle of the rod which is compressed during proximal movement of the. After punching the hole into the vessel, pressure on the handle is removed and the spring expands causing the front of the rod, its associated cylindrical blade and tissue sample to exit from the hollow sleeve.

By virtue of the form of the instrument it is difficult to stabilize it in a constant alignment with the blood vessel. Accordingly, the instrument will change its alignment during its use resulting in poorly defined openings. It is also necessary that large manual forces be applied to the handle of the elongated rod to overcome the pressure of the spring and cut through the vessel wall. This will cause greater or lesser difficulties in accordance the strength of the user.

It has now been found that the above indicated problems may be overcome by use of the punch of the instant invention.

SUMMARY OF THE INVENTION

It is an object of the invention to provide a surgical instrument, to form openings in blood vessels, having an increased mechanical advantage which reduces the manual force requirements.

Another object of the invention is to provide an instrument, as described above, wherein the manual pressure is applied normally to the punch axis thereby stabilizing the punch tip during activation.

Yet another object of the invention is to provide an instrument wherein the removed tissue sample is retained therein for recovery when needed.

According to another object of the invention there is provided a punch wherein the blade has radial serrations to reduce the required cutting force.

These and other objects of the invention will be in part apparent from, and in part suggested by, the detailed description in conjunction with the accompanying drawings.

Throughout this application the terms proximal and rear will be used to refer to points toward or near the user and far or away from the patient and the terms distal or front will be used to refer to points far or away from the user and toward or near the patient.

BRIEF DESCRIPTION OF THE DRAWINGS

The invention is best described in the following detailed description with reference to the drawings, wherein like numbers refer to like parts, in which

FIG. 8 is a right side elevational view, in section, of the blade pusher barrel of the first embodiment.

FIG. 9 is a side elevational view, in section, of the blade drum of the first embodiment.

FIG. 10 is a side elevational view of the punch mandrel of the first embodiment.

FIG. 11 is a top view of the mandrel of FIG. 10.

FIG. 15 is a right side elevational view in section of the blade pusher barrel of the second embodiment of the invention.

FIG. 16 is a top view in section of the blade pusher barrel of the punch of FIG. 12.

FIG. 17 is a sectional view of the blade pusher barrel of the punch of FIG. 12 along line 17—17 of FIG. 16.

FIG. 18 is a sectional view of the blade pusher barrel of the punch of FIG. 12 along line 18—18 of FIG. 16.

FIG. 19 is a sectional view of the blade pusher barrel of the punch of FIG. 12 along line 19—19 of FIG. 16.

FIG. 20 is a side elevational view in section of a third embodiment of the punch of FIG. 1.

DETAILED DESCRIPTION OF THE PREFERRED EMBODIMENT

Figure 1:
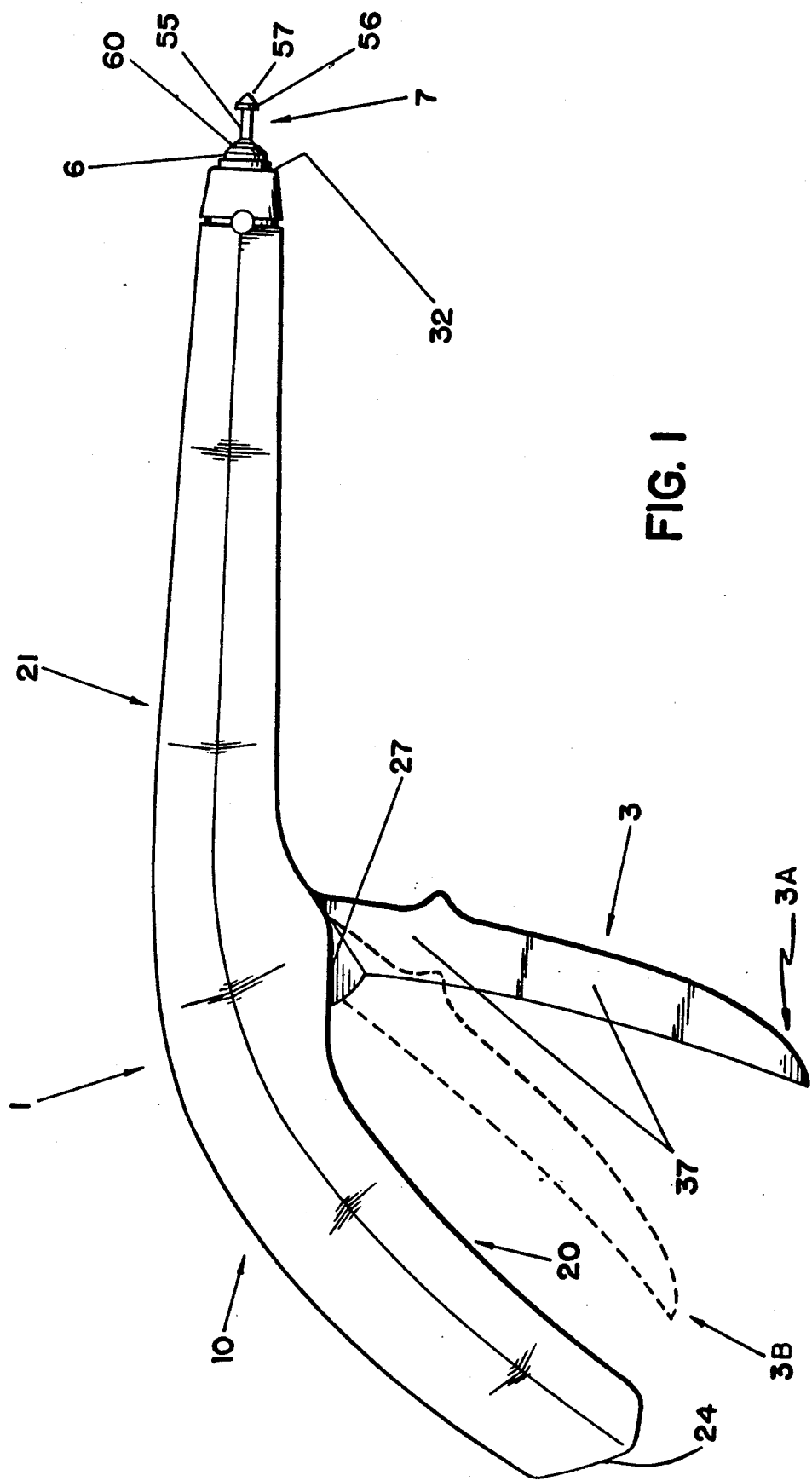
FIG. 1 is a side view of a first embodiment of the invention with its trigger in a forward cocked position.
Figure 2:
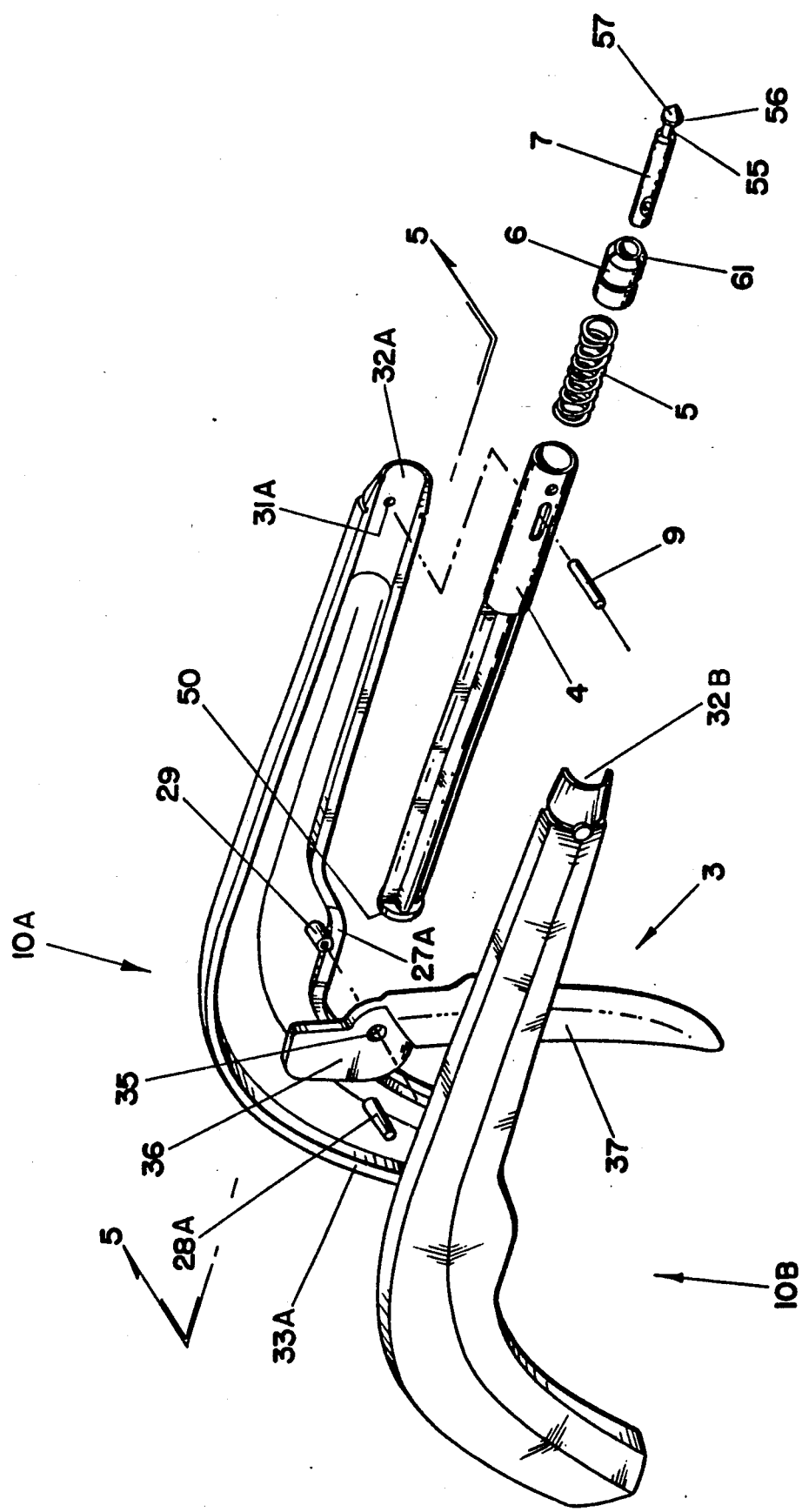
FIG. 2 is an exploded perspective view of the punch of FIG. 1.
Figure 3:
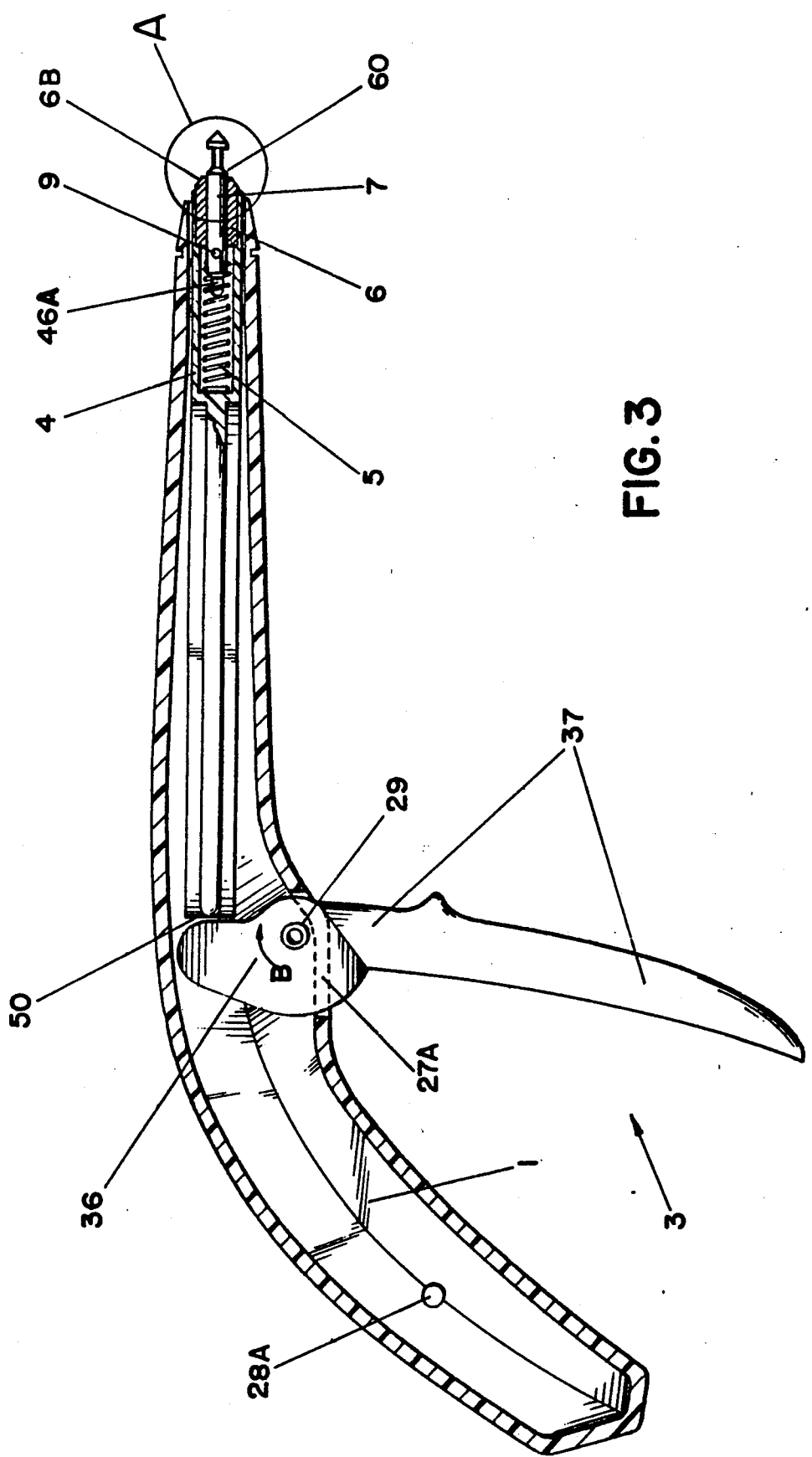
FIG. 3 is a left side elevational view in section of the punch of FIG. 1.

Referring to FIGS. 1–11 the vascular punch, designated by the numeral 1, comprises a pistol-like, closed, hollow housing 10 comprising a proximal, or rear, pistol-like handle portion 20 and a distal, or front, portion 21. The housing also comprises left 10a and right 10b side walls and a flange-like wall 33 (not shown) therebetween at the periphery of the housing from its proximal end to a distal or front opening 32. The punch 1 further comprises a trigger 3 comprising an upper portion 36, illustrated in FIGS. 2, 3 and 7, within the housing 10 and a lower portion, or trigger arm, 37 which extends outside of the housing 10 through a lower port 27, therein, situated at the lower juncture between the proximal 20 and distal 21 sections of housing 10. The trigger arm 37 may occupy two positions, a distal cocked position 3a and a retracted proximal position, illustrated by the dashed lines 3b in FIG. 1. The punch 1 further comprises a blade drum 6 and a punch mandrel 7, as illustrated in FIG. 2. The distal ends of the drum 6 and mandrel 7, as shown in FIGS. 2 and 3, extend distally outside of the housing 10 through the front opening 32 therein.

As shown in FIGS. 2 and 3 punch 1 further comprises a blade pusher barrel 4, a restraining pin 9 and a spring 5. FIG. 2 also illustrates the left 10a, and right 10b, side walls of the housing 10 as well as their associated flange-like portions 33a and 33b (not shown) which combine, on assembly of the punch, to form the flange-like wall 33. The wall 33 which extends from the rear of the housing 10, around its periphery, and terminates at the distal opening 32 and separates the side walls from each other.

In FIGS. 2 and 3 there are also shown means 28a on the inner surface of the left side wall 10a for aligning the two side walls, by coupling said alignment means with complementary means 28b (not shown) on the inner surface of the right side wall 10b during assembly of the punch 1. These alignment means comprise at least one pin 28a extending normally from the inner surface of the proximal portion 20a of the left side wall 10a and an equal number of complementary cavities 28b (not shown) on the inner surface of the right side wall 10b to receive said pin or pins. If desired, the alignment pins may be on the right side wall 10b and the cavities on the left side wall 10a. Other alignment means, as well known in the art, may be used in lieu of the above.

Figure 6:
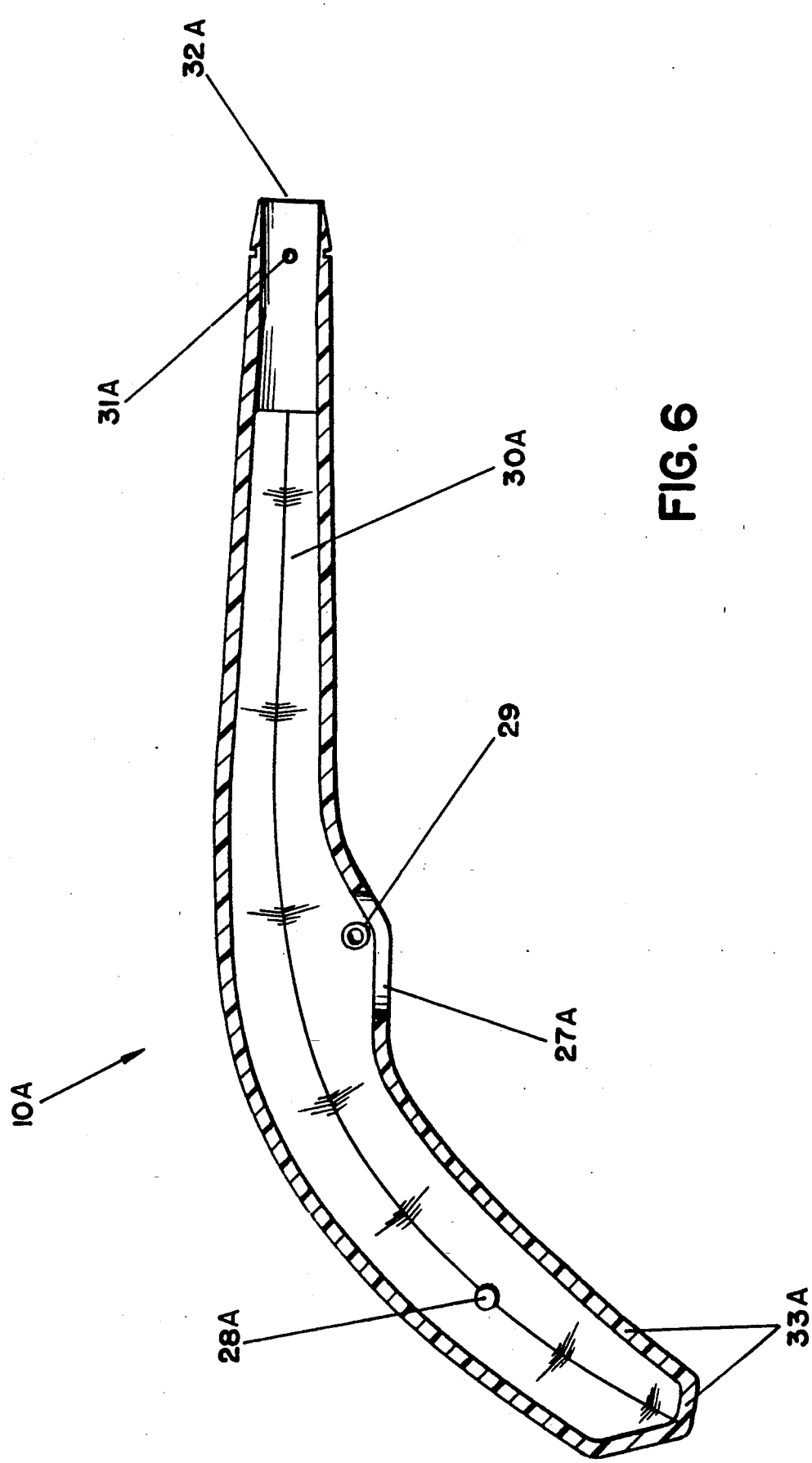
FIG. 6 is a left side elevational view of the left side wall of the punch along line 5—5 of FIG. 2.

The left side wall 10a inner surface further comprises pivot means 29, as shown in FIGS. 2, 3 and 6, for engaging complementary means 35 in the upper portion 36 of the trigger 3 in a pivotal manner. The means 29 consists of a cylindrical pin near the distal portion of a lower opening 27a in flange-like wall portion 33a, of the left side wall 10a, at the lower juncture of the proximal 20a and distal 21a portions thereof. Side wall 10b comprises a similar opening 27b in flange-like wall portion 33b. The openings 27a and 27b combine to form lower opening 27, in the housing 10, when the punch is assembled. If desired, however, said means 29 may be on the inner surface of the right rather than the left side wall of the housing 10. If desired, the pivoting means (not shown) may comprise two pins extending normally from the side walls of the trigger and complementary holes or cavities in the side walls of the housing to receive said pins. In addition, the side walls of the housing 10 comprise, in their distal sections, cavities 31a, in the left side wall, and 31b (not shown) in the right side wall, to receive the restraining pin 9 which has been passed through mandrel 7 to render it immobile during use of the punch.

The distal portion 21 of the housing 10 also comprises a cavity (not shown), to receive the blade pusher barrel 4.

Figure 7:
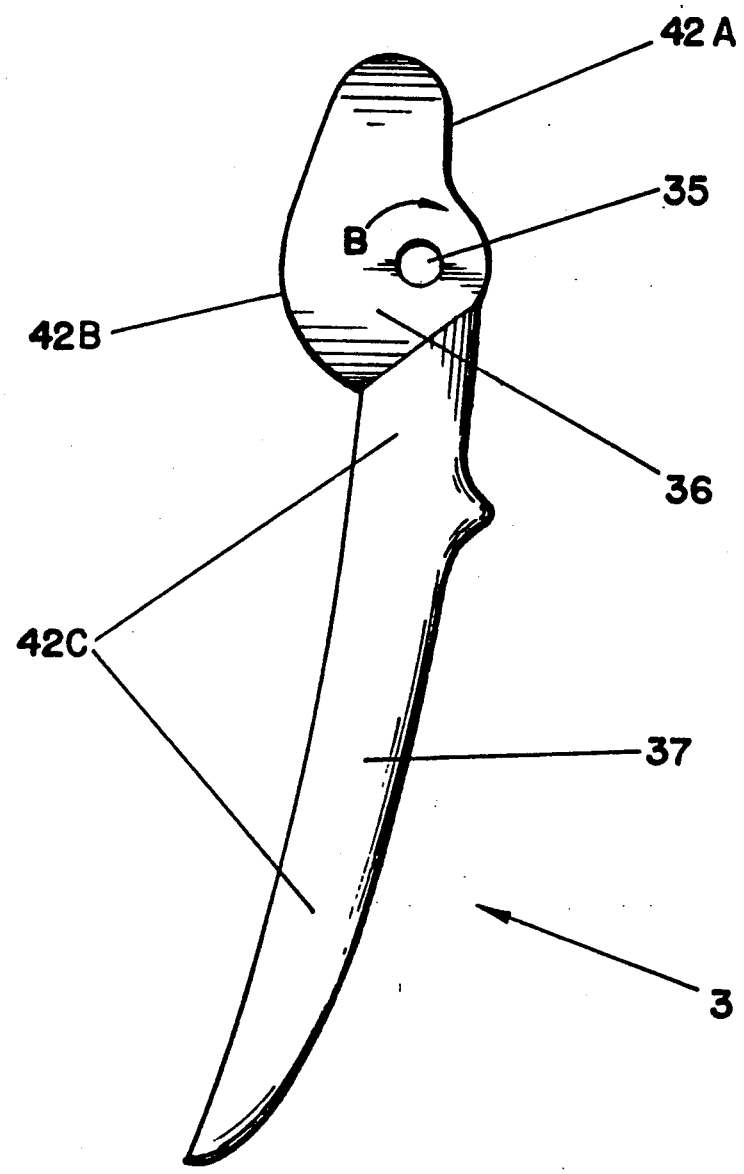
FIG. 7 is a side elevational view of the trigger of the first embodiment.
Figure 12:
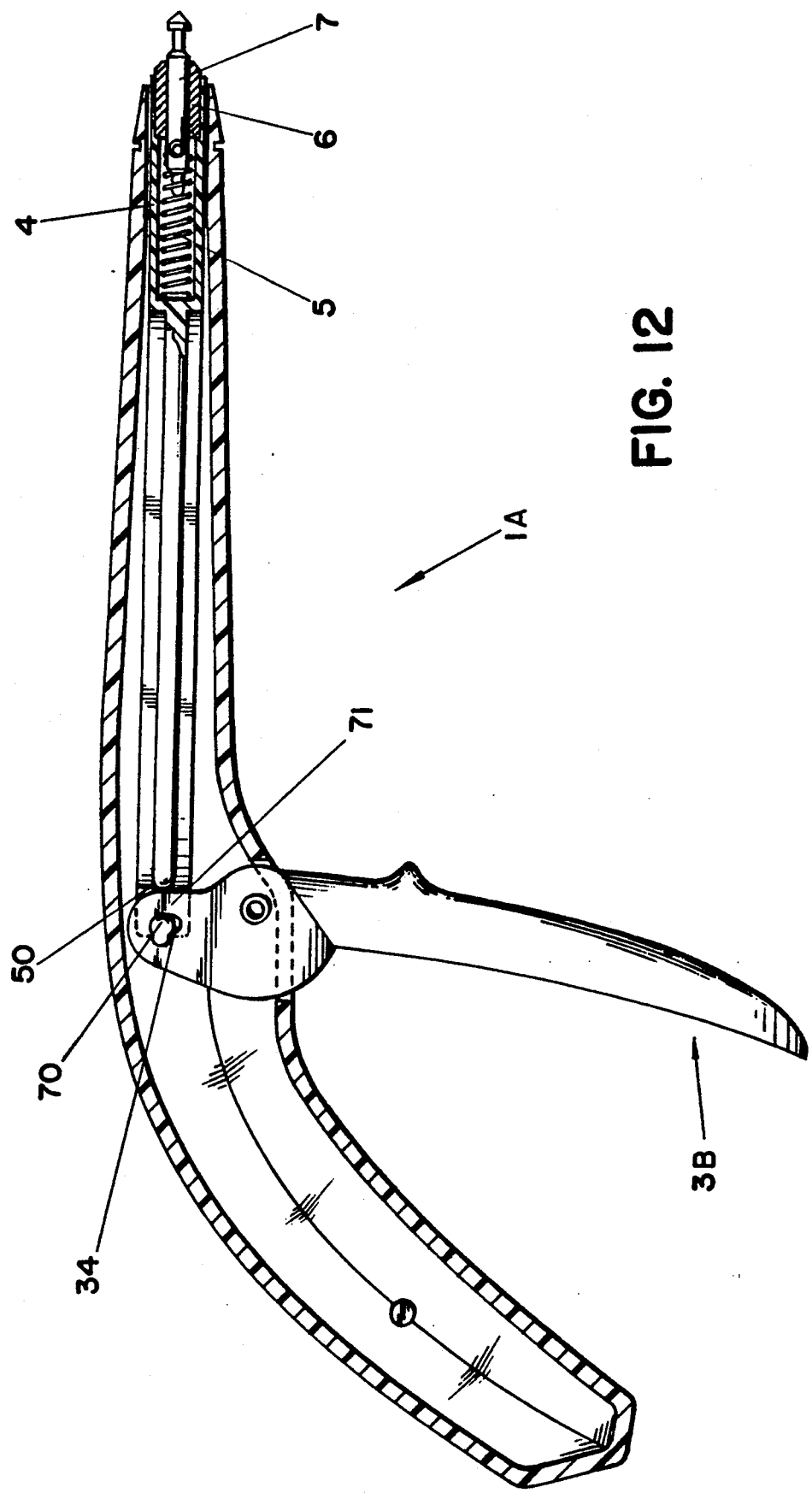
FIG. 12 is a side elevational view in section of a second embodiment of the punch of FIG. 1.
Figure 13:
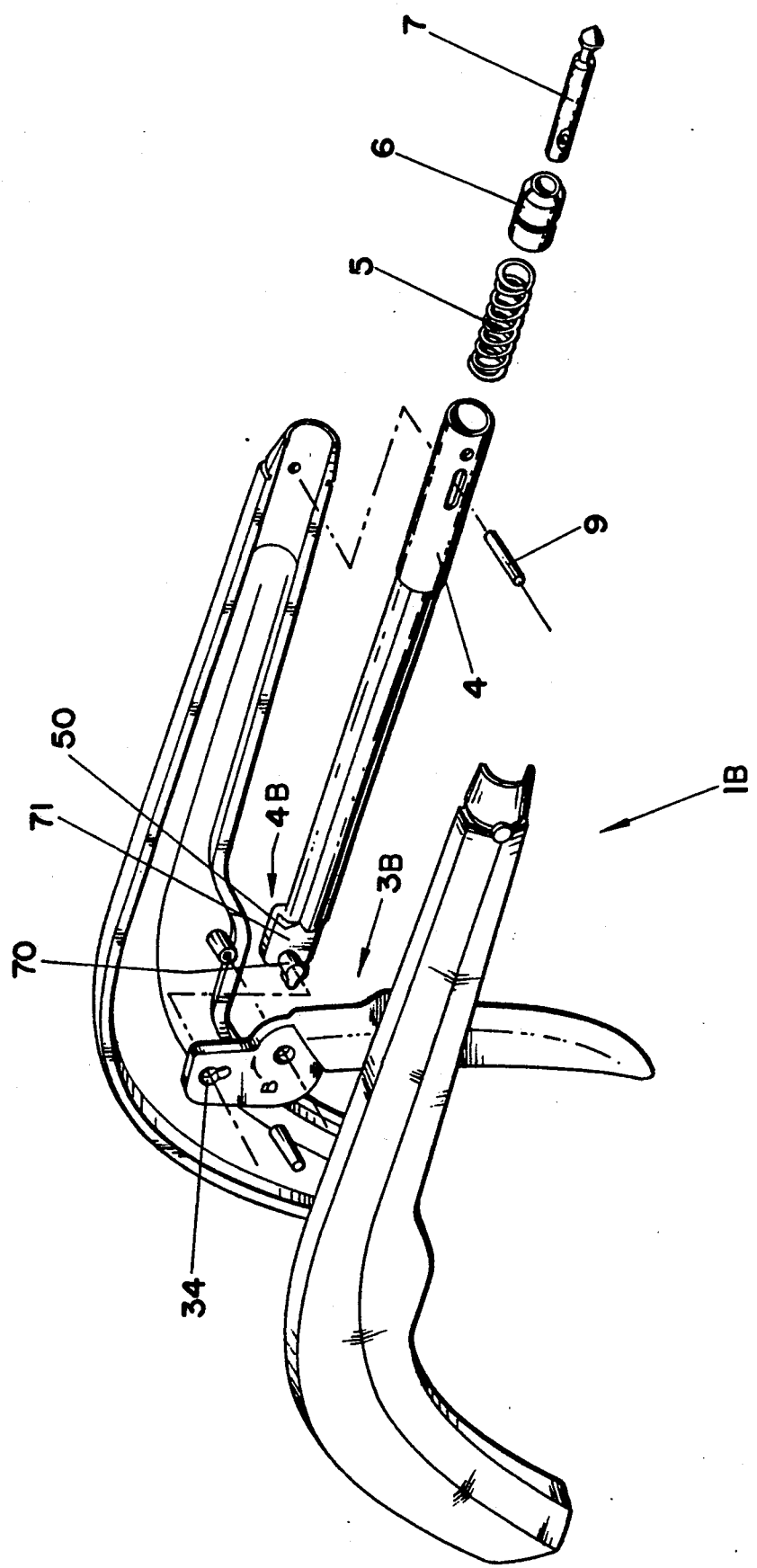
FIG. 13 is an exploded perspective view of embodiment of FIG. 12.

Trigger 3, shown in FIGS. 2, 3, and 7, comprises front 42a, rear 42b and right 42c and left 42d (not shown) side walls and upper 36 and 37 portions. The lower portion 37 comprises a trigger arm for effecting proximal movement of the trigger 3 from its distal 3a to its proximal 3b (dashed lines) position as shown in FIG. 1.

In addition, the trigger upper portion 36 comprises a port 35 therethrough, to engage the pivot pin 29, when the punch is assembled, and allow the trigger 3 to pivot thereabout when the trigger arm 37 is moved proximally during formation of the opening in the blood vessel.

The blade pusher barrel 4, shown in FIGS. 2, 3 and 8, comprises an elongated cylindrical body comprising at its distal end, a cavity comprising a distal portion 52, terminated by a distal opening 43, and a proximal portion 51 terminated by a proximal wall 47.

The inner wall 44 of the cavity portion 52 has an inner diameter slightly greater than the inner diameter of the inner wall 45 of the cavity portion 51.

Proximal wall portion 45 is terminated, where it joins wall portion 44, by a flat wall 53 normal to wall 44. The right and left side walls of blade pusher barrel 4, further comprise elongated slots 46a and 46b (not shown), respectively, spaced proximally from wall 53.

Spring 5, shown in FIGS. 2 & 3, is inserted into cavity portion 51 wherein it is restrained by the restraining pin 9, shown in FIGS. 2 and 3, which has been passed through slots 46a and 46b and received by cavities 31a and 31b of housing 10.

The hollow blade drum 6, shown in FIGS. 3 and 9, comprises an elongated hollow cylinder comprising an outer wall 63, a lumen 65, a rear wall 62, a proximal opening 64 and a distal hollow truncated conical blade portion 61 terminated by an opening 60. The blade drum is inserted into distal cavity portion 52 of the barrel 4 until its rear wall 62 abuts wall portion 53 thereof. The outer diameter of the blade drum outer wall 63 is slightly less than the inner diameter of the barrel cavity portion 52.

Figure 4:
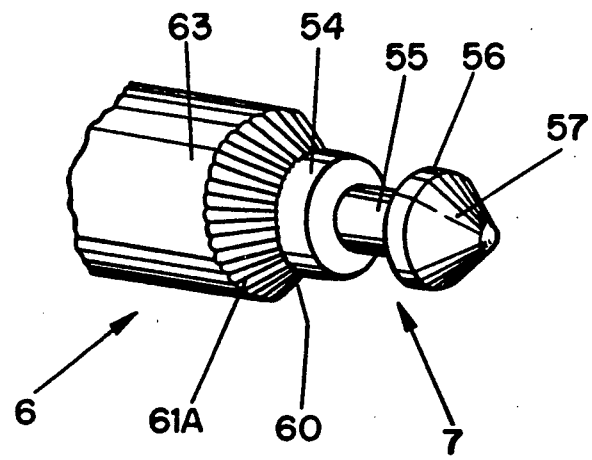
FIG. 4 is a perspective view of a first modification of the portion A in FIG. 3.
Figure 5:
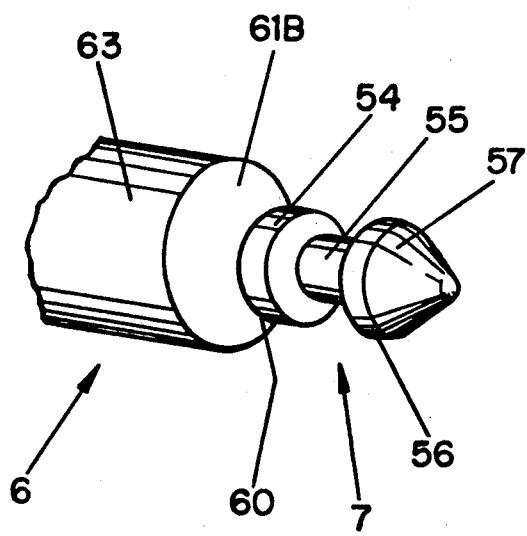
FIG. 5 is a perspective view of a second modification of the portion A in FIG. 3.

In one aspect of this embodiment, illustrated in FIG. 4, the blade portion comprises a serrated knife-edge blade 61a. In a second aspect of this embodiment, as illustrated in FIG. 5, the blade portion comprises a smooth knife-edged blade 61b. In yet another modification, as seen in FIG. 9, the blade portion comprises a flat face 67, which joins the inner surface 68 of the drum at its distal end at an angle of about 90° (i.e., within standard tolerances) to create a sharp cutting edge 69. In this modification the diameter of the disc of the mandrel is less than the inner diameter of the blade drum.

Figure 24:
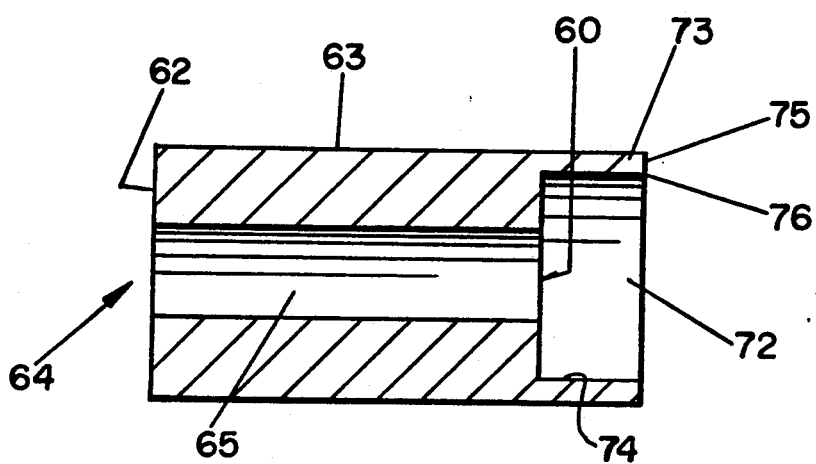
FIG. 24 is a side elevational view, in section, of a modification of the blade drum of FIG. 9.

In another modification of the blade drum, as illustrated in FIG. 24, wherein the diameter of the disc of the mandrel is less than the inner diameter of the blade drum, the distal end of the blade drum comprises a hollow cylindrical portion 72 whose front end comprises a flat face 75 which joins the inner surface 74 of the cylindrical portion 72 at an angle of about 90° to form a sharp cutting edge 75.

The punch mandrel 7, shown in FIGS. 1-5, 10 and 11, is inserted into the blade pusher barrel 4 through the hollow portion 65 of the blade drum 6, the proximal end of the mandrel 7 extending beyond the rear wall 62 of the blade drum 6 into the hollow portion of the spring. The inner diameter of the blade drum cavity 65 is slightly greater than the outer diameter of the mandrel so that the mandrel may pass therethrough.

Mandrel 7, near its proximal end, further comprises a transverse hole 58, therethrough, through which the restraining pin 9, passed through slots 46a and 46b, is also passed. Restraining pin 9 causes the spring to remain proximal to cavity inner wall portion 53. Upon assembly of the punch the ends of restraining pin 9 are received by the cavities 31a and 31b (not shown) of the housing whereby the mandrel 7 is immobilized.

The distal end of mandrel 7 further comprises a reduced diameter stem 55 terminated by a circular disc 56. The disc may have an outer diameter greater than the inner diameter of the blade drum lumen 65, if the disc is to serve as an anvil. Alternatively, the outer diameter of the disc may be less than the inner diameter of the lumen if the disc is to enter the lumen during the hole forming process.

After assembly of the punch, with the trigger 3 in its distal, cocked position, as seen in FIGS. 2 and 3, blade portion 61, of the blade drum 6, will extend distally from opening 32 of the housing 10. It will, however, be spaced proximally from the reduced stem 55 and circular disc 56 of mandrel 7. If desired, the disc 56 may comprise a distal portion 57 comprising a distally tapered truncated cone to facilitate insertion of the disc into the blood vessel.

In the practice of using the vascular punch, of the invention, an incision is made in the blood vessel the length of the incision being smaller than the diameter of the hole to be made therein, and the disc inserted, by means of conical portion 57 (if present) into, the vessel. The proximal side of the circular disc 56 is pulled against the inner wall of the vessel. Pressure is then applied to the trigger arm 37 causing the trigger arm to move proximally toward the handle portion 20 of the housing and pivot about pivot pin 29 whereby trigger upper portion 36 is caused to rotate distally and forward as shown by the arrow B in FIGS. 2, 3 and 7.

As the upper portion 36 of trigger 3 rotates in the direction of arrow B the front face 42a thereof moves forward thereby causing blade pusher barrel 4, whose rear wall 50 abuts the front face 42a of the trigger 3, to move forward whereby blade drum 6 is pushed forward, until the opening 60 of the blade drum 6 abuts the outer wall of the blood vessel opposite the circular disc 56 of mandrel 7. Continued retraction of trigger arm 37 of trigger 3 causes blade 61 to cut a portion out of the vessel and pass over the mandrel reduced stem 55 and circular disc 56 when the inner diameter of the drum is greater than the outer diameter of the disc. After the piece has been cut out it remains on the reduced stem 55 of mandrel 7. The restraining pin 9 prevents movement of the mandrel 7, while blade drum 6 moves forward, thereby causing the reduced stem 55 with its associated tissue sample to be positioned within the cavity 65 in blade drum 6. As blade pusher barrel 4 moves forward the slots 46a and 46b also move forward causing restraining pin 9 to be positioned at the proximal end of the slots. Spring 5 is, consequently, compressed between the rear wall 47 of barrel cavity portion 51 and restraining pin 9. After the hole has been formed in the blood vessel, and pressure on the trigger arm 37 removed, spring 5 expands causing blade pusher barrel 4 and blade drum 6 to move proximally and the trigger arm 37 to move distally. Reduced stem portion 55, of mandrel 7, is then exposed permitting removal of the tissue sample therefrom.

Figure 14:
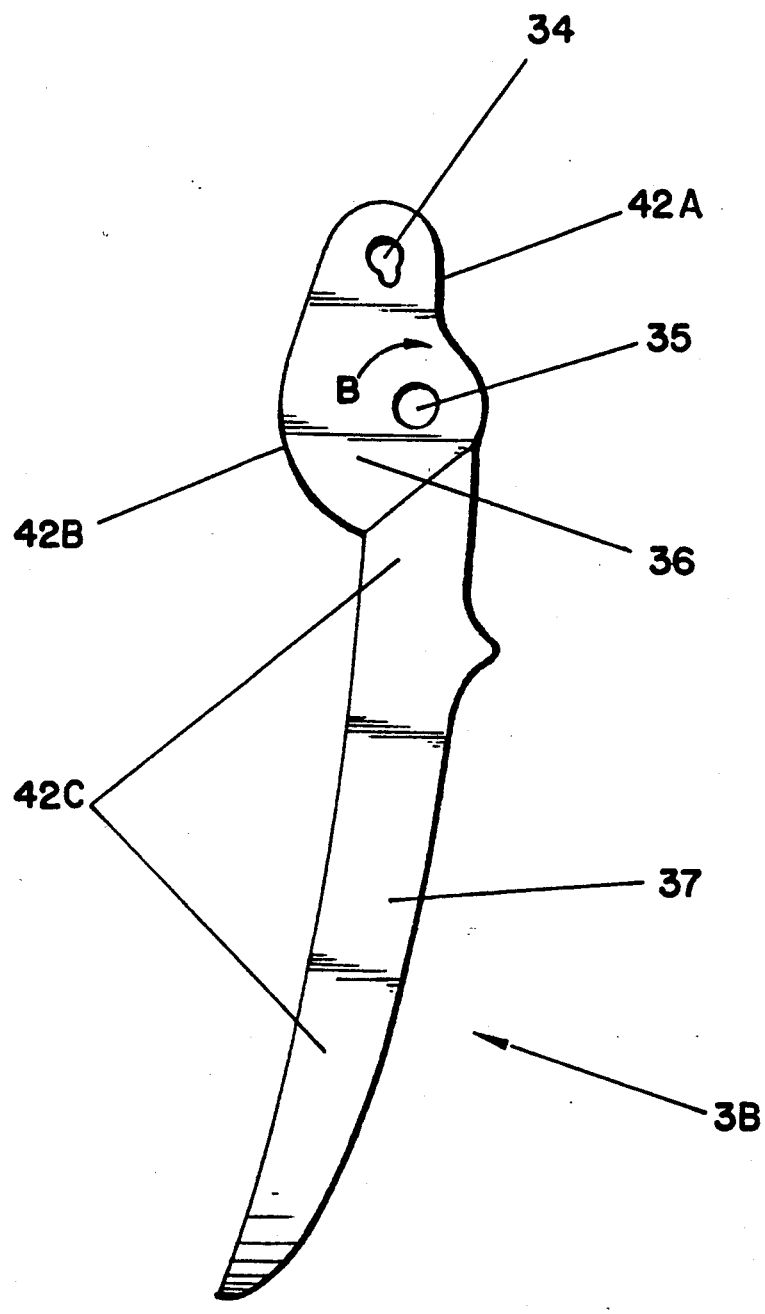
FIG. 14 is a right side elevational view of the trigger of the second embodiment of the invention.

It is sometimes desirable to more accurately control the movement of the blade pusher barrel to prevent misalignment thereof when it is caused to move distally, during the hole forming process, or proximally, after forming the hole. This is accomplished by the second embodiment, designated 1B and illustrated in FIGS. 12-19, of the invention wherein the punch further comprises means for interconnecting the trigger and blade pusher barrel. Thus, trigger 3B, as best seen in FIG. 14, comprises a second hole 34, therethrough, between the side walls 42c and 42d in its upper portion 36. The hole 34 will receive a complementary engaging pin 70 on a modification 4B of the blade pusher barrel 4. In this modification blade pusher barrel 4B, as best seen in FIGS. 15-19, comprises, at its proximal end, a shelf 71 extending proximally and normally therefrom. A cylindrical pin 70, to link the blade pusher barrel 4 to the trigger 3B, through the hole 34 therein, extends normally from said shelf 71. When the barrel and trigger are thusly linked the proximal wall 50 of the barrel abuts the front face 42a of the upper portion 36 of the trigger 3B.

It is, also, often desirable to retain the tissue sample removed from the blood vessel when an opening is formed therein by use of a vascular punch. However, a disadvantage of the prior art punches, which is also present in the above embodiment and modifications of this invention, is the possibility of loss of the tissue samples, from the blood vessels, when the triggers spring back.

That disadvantage is overcome by a third embodiment, designated 1C in FIG. 20, of the invention which provides means for locking the trigger in its proximal, or retracted, position as a consequence of which the reduced stem 55 of the mandrel 7, and the tissue sample, are retained within the lumen 65 of the blade drum 6 until the trigger is intentionally released.

Figure 21:
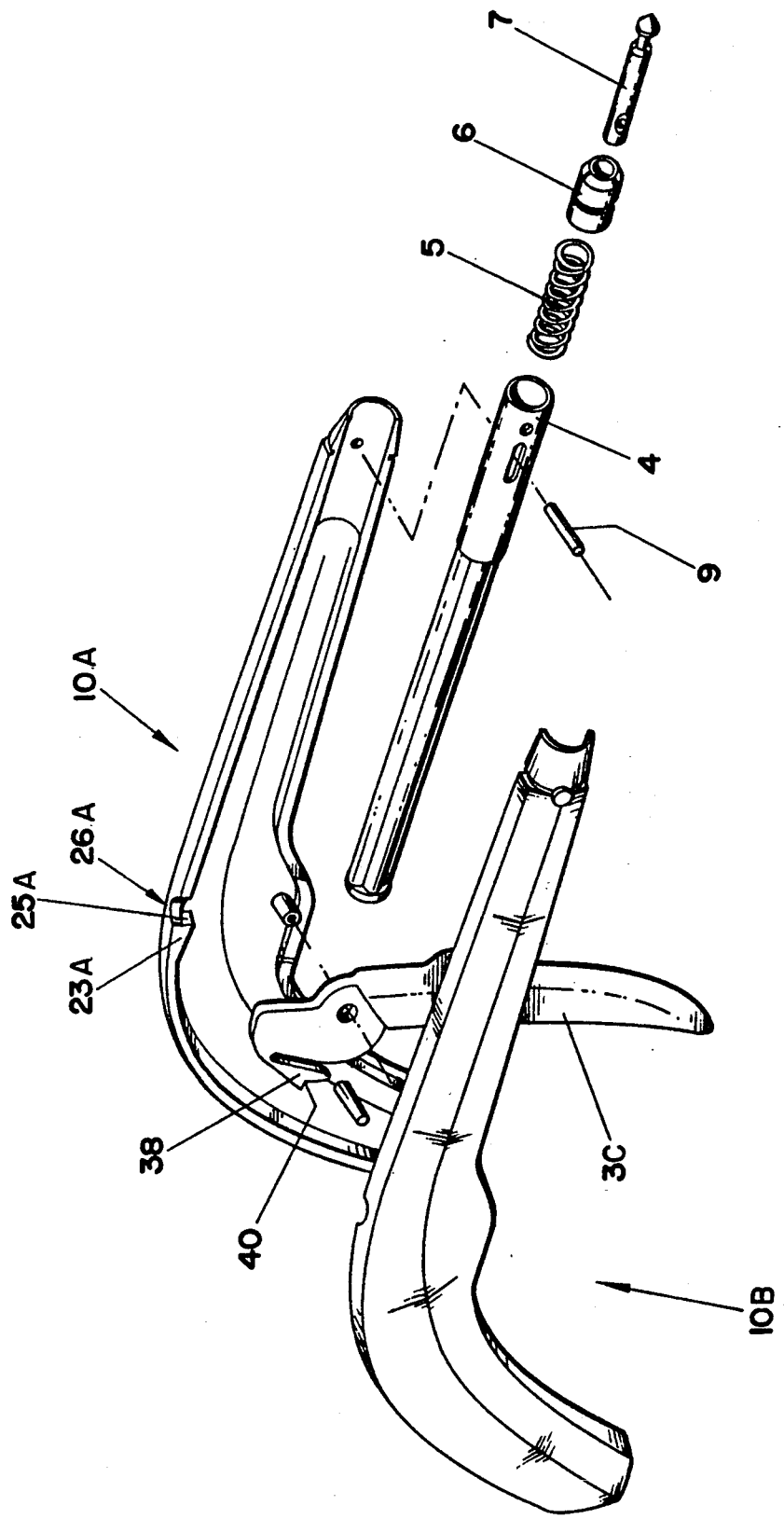
FIG. 21 is an exploded perspective view of the embodiment of FIG. 20.

In this embodiment, as illustrated in FIGS. 20 and 21, the trigger 3C may be locked into a retracted proximal position, as illustrated in FIG. 1, by the dashed lines 3b, through engagement of locking means thereon with complementary locking means in the housing 10. The housing 10 also comprises an upper port through which rigger release means may enter to unlock the trigger 3C when it is in the retracted, locked position 3b.

Figure 22:
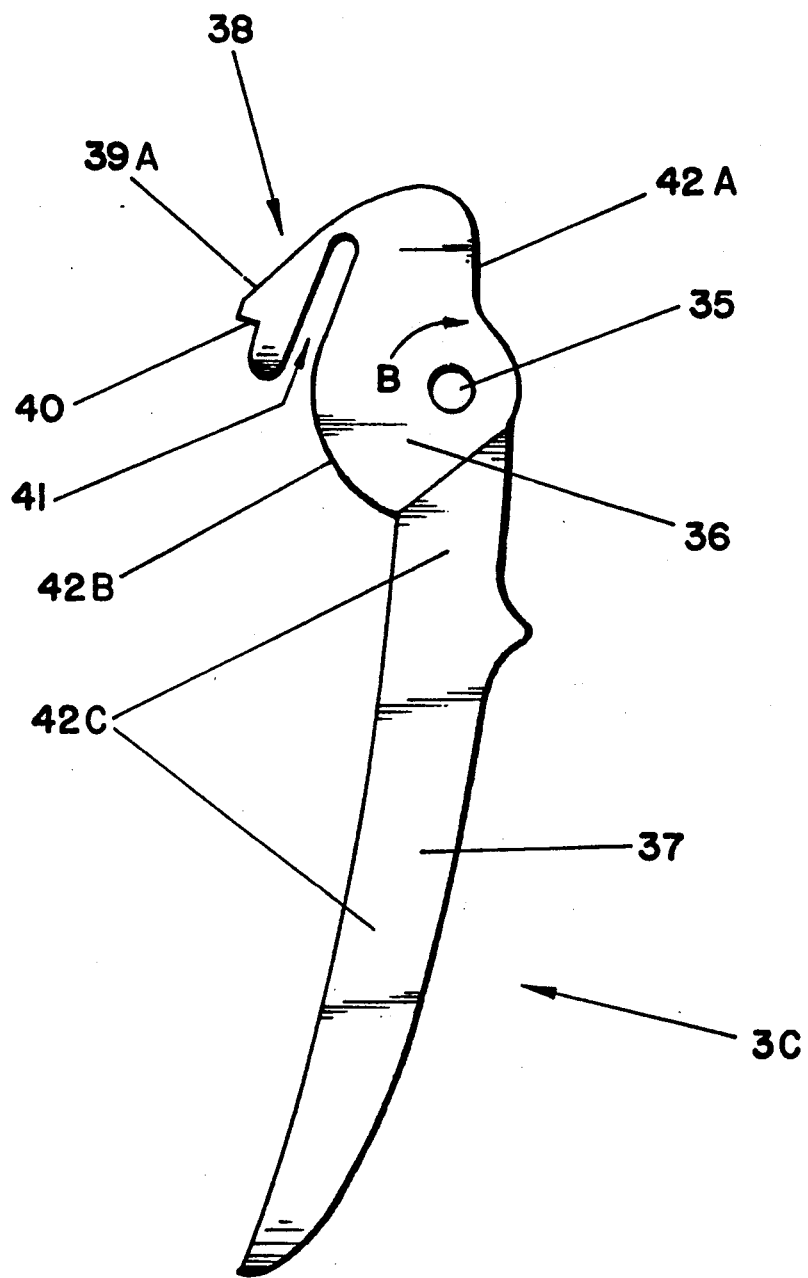
FIG. 22 is a right side elevational view of the trigger of the punch of FIG. 20.

As best seen in FIG. 22 trigger 3C comprises an arm 38, coplanar with the side walls 42c and 42d thereof, which descends, and is separated by a notch 41, from the upper part of the rear wall 42b of the trigger 3C. A protrusion 39, having an angular side wall 39a and bottom flat face 40, which can lockingly engage with complementary locking means of the housing 10, extends from and is coplanar with arm 38. The distal rotation of trigger upper portion 36, during cutting of the hole in the blood vessel, causes arm extension 39 to move upward along a complementary angular wall 24 (not shown) of locking means 23 (not shown) on the flange-like wall 33 (not shown) of the housing 10 thereby causing notch 41 to close. At the greatest extent of proximal retraction of the trigger arm 37 of trigger 3C, the lower end of arm 38 passes the upper end of locking means 23 and notch 41 springs open causing face 40 on arm 38 and the upper face 25 (not shown) of the locking means 23, on housing 10, to lockingly engage. Trigger arm 37 of trigger 3C, therefore, cannot be caused to involuntarily move distally. Consequently, blade drum 6 cannot be retracted and the distal end of the mandrel 7 with the tissue sample attached to the reduced stem 55 thereof will not extend beyond the opening 60 of blade drum 6. Thus, the tissue sample cannot fall off and is protected until its recovery is desired. The angular wall 24 and upper face 25 of the locking means 25 and the flange like wall 33 of the housing are formed from their corresponding parts, e.g., angular wall portions 24a and 24b (not shown) on the right and left side walls 10a and 10b, respectively, of the housing.

Figure 23:
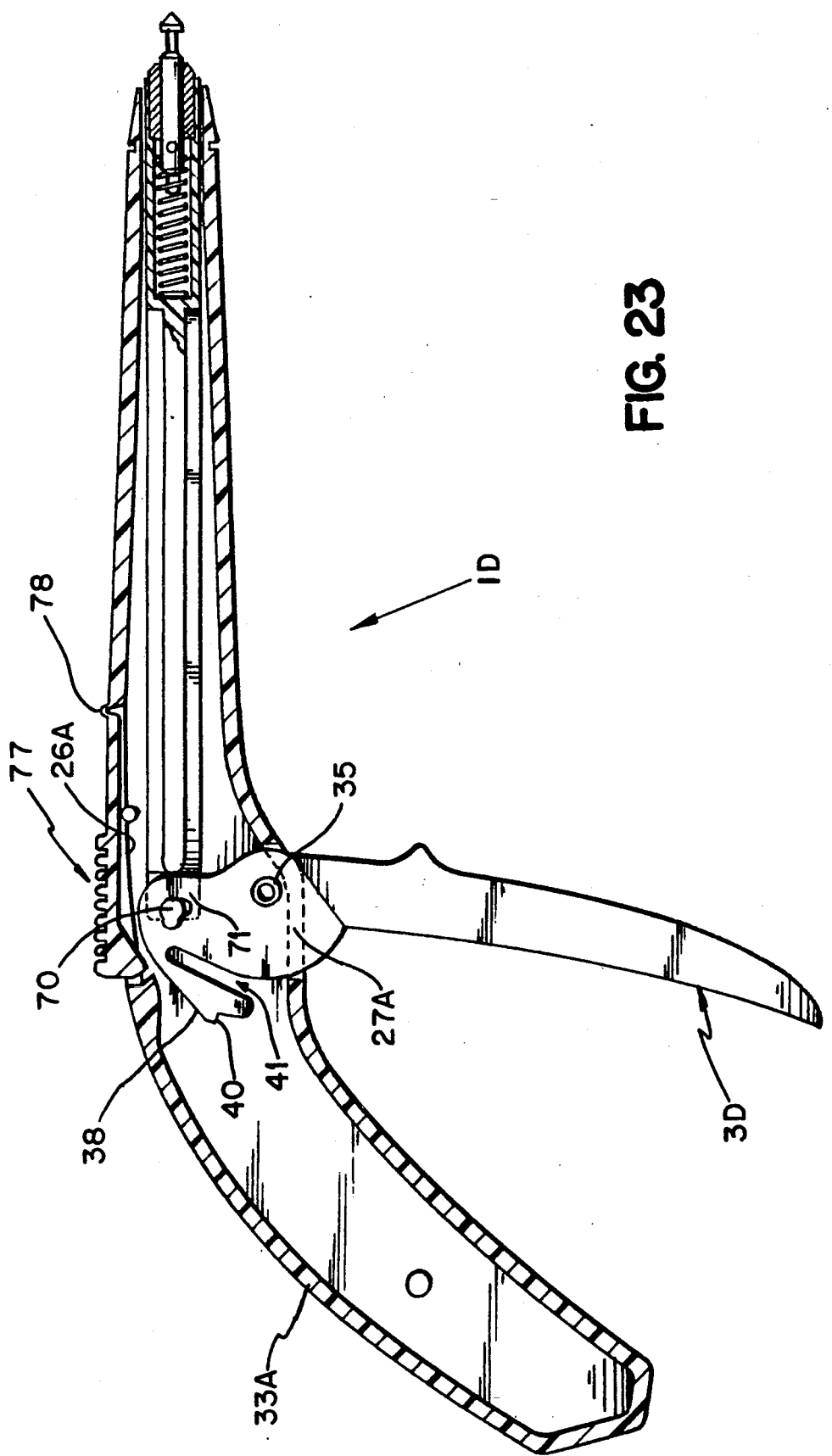
FIG. 23 is a side elevational view in section of a fourth embodiment of the punch of FIG. 1.

When removal of the tissue sample is desired trigger release means, such as the tip 66 of a cap 8, as shown in FIG. 20, is inserted through upper port 26 of the housing until it engages arm 38. Continued downward pressure of the tip 66 causes arm 38 to move toward the trigger 3C body forcing notch 41 to close. Upon closure of notch 41 the complementary locking means on the trigger 3C and housing 10 disengage. Spring 5 then expands causing blade pusher barrel 4 and blade drum 6 to move proximally while the trigger arm 37 of trigger 3C moves distally. Reduced stem portion 55, of mandrel 7, is then exposed permitting removal of the tissue sample therefrom. In a most preferred embodiment the release means comprises an cantilever type tab 77, as seen in FIG. 23, on the top of the housing and attached to the port 26 at its distal side wall 78. If desired, the tab 77 may be an integrally molded part of the housing. The tab 77 can be pressed downward thereby releasing the locking means by compressing the notch 41 and causing the locking arm 38, on the trigger, and the complementary protrusion 23 of the housing to disengage. Other release means, as known in the art, may be used in lieu of the above indicated means.

In a fourth embodiment, designated 1D and illustrated in FIG. 23, the vascular punch 1 of the first embodiment further comprises the trigger - blade pusher barrel linking combination of the second embodiment and the trigger locking and release features of the third embodiment. In this embodiment all of the parts act in the same manner, as described above, as similarly designated parts in the other embodiments.

Changes may be affected with respect to the details of construction and use of the invention without departing from the spirit and scope thereof as defined in the appended claims.

I claim

1. A vascular punch for cutting openings in blood vessels comprising a pistol-shaped housing having an opening at the front end thereof; a blade drum provided at said opening of said housing; a punch mandrel having an end thereof passing through said opening in said housing; a trigger having an arm pivot means for pivoting said trigger on said housing, said housing having port means through which said trigger arm of said trigger can extend outwardly; restraining means in said housing for engaging said punch mandrel; and blade pusher barrel means movably mounted between said trigger and said blade drum, said trigger further comprising a lower portion extending outside of said housing; and an upper portion residing within said housing comprising means for transferring motion to said blade pusher barrel means, said blade pusher barrel means being axially and reciprocally movable within barrel receiving means of said housing, and comprising an elongated cylindrical body comprising means for receiving motion transferred from the upper portion of said trigger, cavity means to contain said blade drum and said punch mandrel, opposing elongated longitudinal slots through which said punch mandrel restraining means passes to engage said punch mandrel, said punch mandrel further comprising an elongated cylindrical rod having a transverse hole therethrough to receive said punch mandrel restraining means and a reduced stem at its distal end terminated by a circular mandrel disc normal thereto, said blade drum comprising a hollow cylindrical body having a longitudinal lumen for passage of said punch mandrel therethrough; and blade means for cooperating with said circular disc of said punch mandrel to form said opening in the blood vessel, said restraining means preventing movement of said punch mandrel when said blade pusher barrel means and said blade drum move axially and reciprocally; and restoring means for restoring said trigger to a normal position after use.

2. A punch of claim 1, wherein said housing comprises
   a. pistol shaped side walls;
   b. means for aligning said side walls during assembly; and
   c. pivot means, comprising a pin normal to, and on the inner surface of, one of said side walls, to engage complementary pivoting means on the trigger.

3. The punch of claim 1, wherein the upper portion of said trigger comprises
   1) a hole passing therethrough, from one side wall to the other, to engage said pivot means of said housing around which said trigger may pivot; and
   2) a front wall which abuts the rear wall of said blade pusher barrel.

4. The punch of claim 1, wherein said blade pusher barrel comprises an elongated cylindrical body comprising:
   a. a front end having a cavity; comprising
      1) a port at its front end;
      2) a distal hollow section to receive said blade drum;
      3) a proximal hollow section, adjacent said distal hollow section, to receive said spring means and having an inner diameter which is less than the inner diameter of said distal hollow section; and
      4) a rear wall; and
   b. a rear end comprising
      1) a wall perpendicular to the longitudinal axis of the barrel;
      2) two opposing longitudinal slots through the walls of said proximal hollow section adjacent said distal hollow section, through which said restraining pin passes; and
      3) a flat wall at, and normal to, said front end of the proximal hollow section which abut said rear wall of said blade drum.

5. The punch of claim 1, wherein the outer diameter of said mandrel disc is slightly less than the inner diameter of said blade drum.

6. The punch of claim 1, wherein the outer diameter of said mandrel disc is slightly greater than the inner diameter of said blade drum.

7. The punch of claim 1, wherein the front portion of said blade drum comprises a truncated cone the distal portion of which forms said blade.

8. The punch of claim 7, wherein said blade is a serrated-edged knife blade.

9. The punch of claim 7, wherein said blade is a smooth bevel-edged knife blade.

10. The punch of claim 7, wherein the front wall of said blade drum comprises a flat face which joins the inner surface of said drum at an angle of about 90 degrees to form a sharp cutting edge.

11. The punch of claim 1, further comprising complementary locking means on said housing and trigger for releasably locking said trigger arm in its proximal, retracted position whereby said reduced stem of said punch mandrel, with its associated circular disc, is retained within said blade drum cavity, and releasing means to cause said complementary locking means to disengage.

12. The punch of claim 11, wherein said complementary locking means on said trigger comprises an arm, descending from a rear wall of the upper part of the trigger, coplanar with the side walls, the lower portion of said arm being separated from said rear wall of the trigger by a compressible notch, said arm further comprising means to lockingly engage complementary means on said housing and releasing means to selectively and manually compress said locking arm notch thereby urging said complementary locking means to move apart and become disengaged.

13. The punch of claim 12, wherein said releasing means comprises
   a. an upper port in said housing adjacent said locking arm of said trigger; and
   b. an article which may be passed through said port to press upon said locking arm and compress said notch.

14. The punch of claim 12, wherein said releasing means comprises a molded portion of said upper housing wall adjacent said locking arm of said trigger which can be depressed, whereby it can press on said trigger locking arm and thereby compress said notch.

15. A vascular punch, for cutting openings in blood vessels, comprising:
   a. a substantially closed pistol-shaped housing comprising:
      1) two pistol shaped side walls, each comprising a pistol grip shaped descending proximal section and an approximately horizontal barrel shaped distal section;
      2) a flange-like wall, extending normally to and peripherally around the edges of said side walls from the proximal end of the housing to a distal end thereof;
      3) an opening at said distal end through which a punch mandrel and a blade drum pass through;
      4) a lower port, near a lower juncture of said proximal and distal sections thereof, through which a trigger passes through;
      5) pivot means around which an upper portion of said trigger may rotate;
      6) two matching cavities, in said side walls, spaced from said front opening of said housing, engaging a restraining pin which passes through slots in a blade pusher barrel and a transverse hole in said punch mandrel;
      7) matching cavities in said distal section of said side walls which combine to form a cavity in the assembled housing to receive said blade pusher barrel;
      8) at least one pin normal to the inner surface of one side wall, extending from said side wall into said housing; and
      9) at least one complementary cavity on the inner surface of the other side wall to receive said at least one pin for alignment and coupling to form the assembled housing;
   b. said trigger comprising;
      1) a lower portion forming a trigger arm, extending outwardly from said housing;
      2) an upper portion residing within said housing comprising;
         a) front, rear and side walls;
         b) means complementary to said pivot means in the housing around which said trigger may pivot,
         said front wall of said trigger abutting against a rear wall of said blade pusher barrel; and
         c) said blade pusher barrel, being axially movable within said housing, and comprising an elongated cylindrical body comprising;
      1) at its front end a cavity comprising;
         a) a front opening;
         b) a distal hollow section to receive said blade drum; and
         c) a proximal hollow section, adjacent said distal hollow section, whose inner diameter is less than the inner diameter of said distal hollow section;
      2) a wall at its rear end perpendicular to the longitudinal axis of said barrel;
      3) two opposing longitudinal slots through the walls of the proximal hollow section, adjacent its junction with the distal hollow section, through which said restraining pin passes; and
      4) a flat wall at, and normal to, said distal end of said proximal hollow section to abut the rear wall of said blade drum;
         d) said punch mandrel comprising an elongated cylindrical rod comprising;
      1) hole therethrough spaced distally from said proximal end to receive said restraining pin;
      2) a reduced stem at its distal end terminated distally by a circular disc normal thereto;
         e) said blade drum means comprising a hollow cylindrical rod comprising;
      1) a longitudinal concentric lumen for passage of the punch mandrel therethrough;
      2) blade means to cooperate with said circular disc of said punch mandrel to form a hole in a blood vessel; and
      3) at its proximal end, a flat rear wall perpendicular to the longitudinal axis of said rod, wherein the outer diameter of said wall is slightly greater than the inner diameter of said proximal cavity portion, and slightly less than the inner diameter of said distal cavity portion, of said blade pusher barrel;
         f) said restraining pin comprising an elongated cylindrical rod whose outer diameter is slightly less than the inner diameter of aid transverse hole in the rear end of said punch mandrel; and
         g) spring means inserted in said proximal portion of said cavity of said blade pusher barrel and restrained therein by said restraining pin passing through said punch mandrel.

16. The punch of claim 15, wherein said blade means comprises a distal truncated cone.

17. The punch of claim 16, wherein said blade means comprises a smooth knife-edged blade.

18. The punch of claim 6, wherein said blade means comprises a serrated blade.

19. The punch of claim 16, wherein the front wall of said blade drum comprises a flat face which joins the inner surface of said drum at an angle of about 90 degrees to form a sharp cutting edge.

20. The punch of claim 15, further comprising locking means in said housing for lockingly engaging complementary means on the side arm of the upper portion of said trigger when said trigger arm is in its proximal position, said blade drum extending outside of said housing and said reduced stem and circular disc of said punch mandrel is retained in said blade drum lumen and trigger releasing means for selectively and manually compressing said trigger arm notch, thereby urging said complementary locking means to move apart and become disengaged.

21. The punch of claim 20, wherein said locking means on said trigger comprises an arm, descending from the rear wall of the upper part of said trigger, coplanar with said side walls, the lower portion of said arm being separated from said rear wall of said trigger by a compressible notch, said arm further comprising means to lockingly engage complementary means on said housing.

22. The punch of claim 21, wherein said trigger releasing means comprises
    a) an upper port in said housing adjacent said locking arm of said trigger; and
    b) an article which may be passed through said port to press upon said locking arm and compress said notch.

23. The punch of claim 21, wherein said releasing means comprises a molded portion of the upper housing wall adjacent said locking arm of said trigger which can be depressed, whereby said molded portion presses on said trigger locking arm to thereby compress said notch.

24. The punch of claim 15, wherein said circular disc terminating the front end of said punch mandrel has a larger outer diameter than the inner diameter of said blade drum.

25. The punch of claim 15, wherein said circular disc terminating the front end of said punch mandrel has a smaller outer diameter than the inner diameter of said blade drum.

26. The punch of claim 15, further comprising linking means for linking said blade pusher barrel to said trigger.

27. The punch of claim 26, wherein said linking means comprises
    a) a shelf whose top surface is coplanar with said trigger side walls, extending proximally from said rear wall of the blade pusher barrel, said shelf further comprising an elongated pin extending normally from said top surface to engage complementary means on said trigger; and
    b) a hole on said trigger upper portion, extending therethrough from one side wall, to engage said pin.

28. The punch of claim 15, wherein the pivoting means
    a) on said housing comprises a pin attached to the inner surface of one side wall of said housing extending approximately normally into the housing around which the upper portion of the trigger may rotate; and
    b) on said trigger comprises a hole to engage said pin.

29. The punch of claim 15, wherein said pivoting means
    a) on said trigger comprises at least one pin extending normally from at least one side wall thereof; and
    b) on said housing comprises at least an equal number of complementary pin receiving means in the side walls thereof.

30. The punch of claim 1, further comprising linking means for linking said blade pusher barrel to said trigger.

31. The punch of claim 30, wherein said linking means comprises
    a) a shelf whose top surface is coplanar with said trigger side walls, extending proximally from the rear wall of said blade pusher barrel, said shelf further comprising an elongated pin extending normally from said top surface to engage complementary means on said trigger; and
    b) a hole on said trigger upper portion, extending therethrough from one side wall, to engage said pin.

32. The punch of claim 1, wherein said pivoting means
    a) on the housing comprises a pin attached to the inner surface of one side wall of said housing extending approximately normally into said housing around which the upper portion of the trigger may rotate; and
    b) on said trigger comprises a hole to engage said pin.

33. The punch of claim 1, wherein said pivoting means
    a) on said trigger comprises at least one pin extending normally from at least one side wall thereof; and
    b) on said housing comprises at least an equal number of complementary pin receiving means in the side walls thereof.

34. The punch of claim 1, wherein the front portion of said blade drum comprises a cylinder, the inner diameter of which is greater than the diameter of said mandrel disc, and whose distal face joins the inner surface of the drum at an angle 90 degrees to form a sharp cutting edge.

* * * * *